United States Patent [19]

Epley

[11] 3,995,620
[45] Dec. 7, 1976

[54] AIR CALORIC DELIVERY TUBES

[75] Inventor: John M. Epley, Portland, Oreg.

[73] Assignee: Instrumentation & Control Systems, Inc., Addison, Ill.

[22] Filed: Nov. 5, 1975

[21] Appl. No.: 629,021

[52] U.S. Cl. .............................. 128/2 R; 128/2 N; 128/2.1 M; 128/401
[51] Int. Cl.² ........................................ A61B 19/00
[58] Field of Search ............ 128/2.1 M, 2.1 R, 2 R, 128/2 N, 2 T, 2 Z, 240, 241, 255, 184, 401, 245

[56] References Cited
UNITED STATES PATENTS

| 989,839 | 4/1911 | Fowler | 128/241 |
|---|---|---|---|
| 1,591,410 | 7/1926 | Spang | 128/241 |
| 3,000,271 | 9/1961 | Harvey et al. | 128/2.1 M |
| 3,563,231 | 2/1971 | Ducote | 128/2.1 M |
| 3,636,940 | 1/1972 | Gravlee | 128/241 |
| 3,794,017 | 2/1974 | Servos | 128/2.1 M |
| 3,882,848 | 5/1975 | Klar et al. | 128/2 Z |

FOREIGN PATENTS OR APPLICATIONS 598,258  9/1959  Italy ................................ 128/2 Z Primary Examiner—Robert W. Michell
Assistant Examiner—Lee S. Cohen
Attorney, Agent, or Firm—Alter and Weiss

[57] ABSTRACT

Delivery tubes used with air caloric stimulation systems, when measuring vestibular responses. The delivery tubes fit into the patient's ears at the nozzle end thereof. Silastic tubing is provided narrower at the nozzle end for forming a higher velocity narrower stream of air directed at the tympanic membrane to produce more effective and consistent heat exchange with the labyrinth. A shield is provided to prevent the tubing from impinging on the tympanic membrane and to retain the apparatus in place. A handle is also provided to aid in the insertion of the delivery tube into the air canal, and to aid in attaching the delivery nozzle of the delivery head regularly used with the air caloric stimulation system.

6 Claims, 7 Drawing Figures

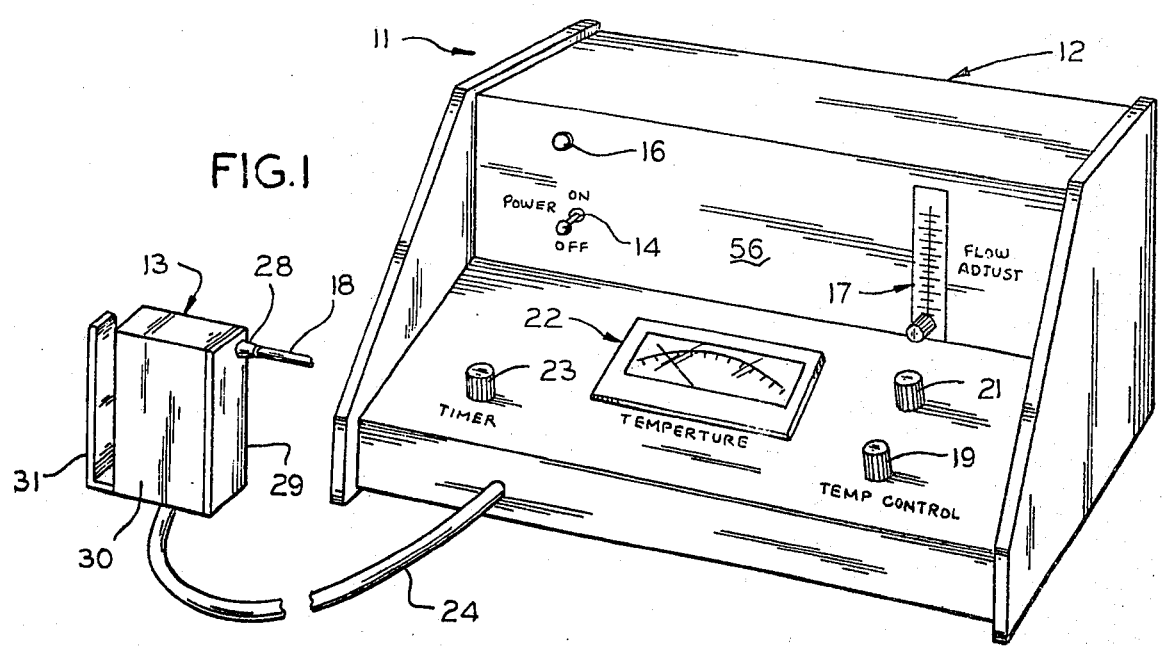
FIG.1
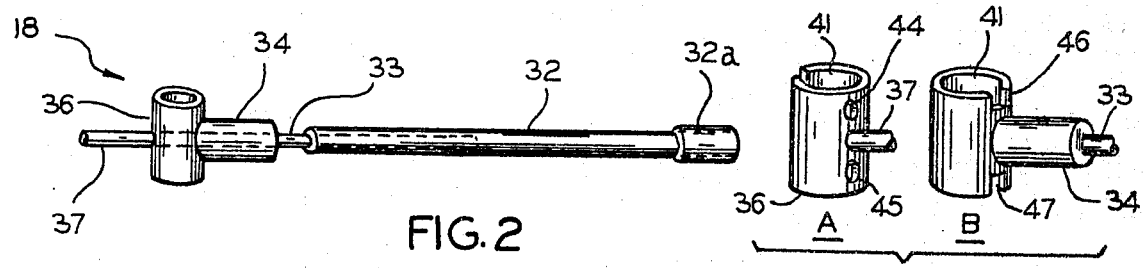
FIG.2
FIG.5
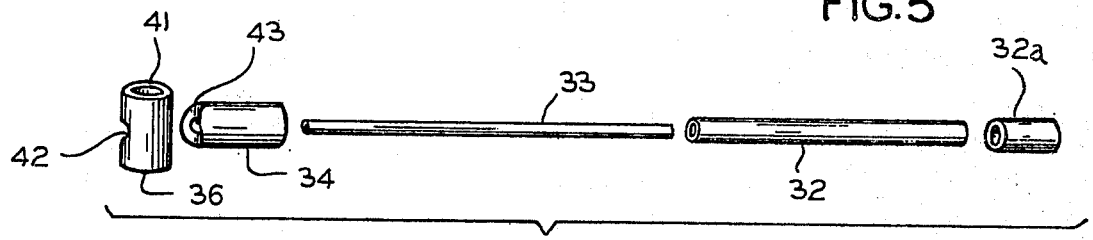
FIG.3
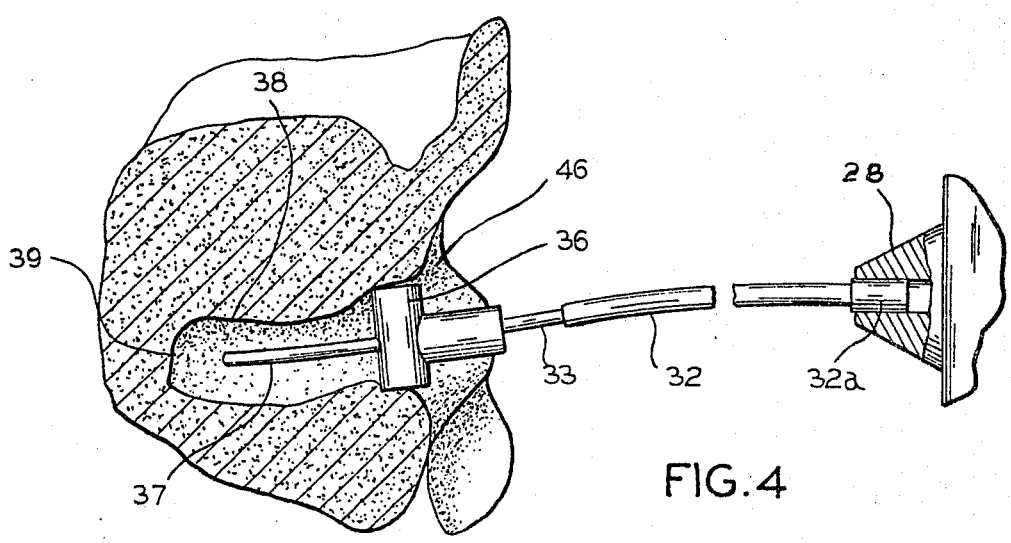
FIG.4

AIR CALORIC DELIVERY TUBES

This invention relates to systems used for measuring vestibular responses on the human body, by controlling the flow and temperature of air used in eliciting a nystagmus response, and more particularly, to air caloric delivery tubes which actually are placed in the patient's ear during the nystagmus measurements.

Caloric testing used in eliciting nystagmus responses has developed into an indispensible, integral part of the clinical evaluation of a patient's equilibritory and vertiginous disorders. Such testing enables the otoneurologist to assess the functional status of each ear separately by measuring the reflex responses generated by thermal stimulation of the non-auditory labyrinth of the ear. Originally ice-water caloric tests were employed to determine nystagmus responses. Subsequently, temperature controlled water was used to elicit the nystagmus responses. Still more recently, thermally controlled air has been used as a stimulating means.

When the air has been delivered to the ears in the past, simple plastic tubes have been used. A plurality of difficulties were encountered when using simple plastic tubes. Among these difficulties was the inefficient use of the delivery air because the prior art delivery tubes failed to direct the air onto the tympanic membrane and enabled a large amount of air to escape without affecting the temperature of the inner labyrinth of the ear, thereby requiring a greater flow with inconsistent effect. The depth and position of tube placement was also inconsistent.

In the past, the tympanic membrane has often sustained pain because of impingement when placing the delivery tube into the outer ear. This last named problem arises because the delivery tubes provided until now have been relatively stiff to self-maintain the delivery tube in the patient's ear without having to actually hold it there. Thus, a related problem is to maintain the delivery tube in the ear, while the air is delivered for test purpsoses.

Accordingly, an object of the present invention is to provide new and unique air caloric delivery tubes for use in air caloric stimulation systems when measuring vestibular responses.

A related object of the present invention is to provide air caloric delivery tubes that are self-maintained in the patient's ear during the delivery of the air.

Yet another object of the present invention is to provide air caloric delivery tubes which are sufficiently soft to conform to the contour of the ear canal.

Still another and related object of the present invention is to provide a handle means for aiding in the insertion of the air caloric delivery tubes into the ear canal, and also for attaching the delivery tubes to the air caloric nozzle on the head of the nystagmus equipment.

Yet another object of the present invention is to provide means for increasing the velocity of the air stream and directing it at the tympanic membrane so that the temperature difference can be more effectively and consistently conducted to the labyrinth.

This is accomplished by having narrower tubing in the ear canal, than at the head. This provides a nozzle effect and results in a narrower, higher velocity directed air stream.

A preferred embodiment of the inventive delivery tube includes a silastic tubing, one end of which has a smaller inner diameter than the other end. The end with the smaller diameter is attached to the end with the larger diameter by using either interfacing tubing or by inserting the smaller diameter tube into the larger diameter tube. The larger diameter tube is fitted into the air caloric nozzle on the head of the air caloric delivery system by means of a sleeve which is harder plastic to facilitate insertion.

Means are provided for assuring that the depth of application of the tubing into the ear is the same for both ears and on repeated tests. More particularly, a shield is provided to perform two other functions. One is to assure that the actual delivery tube extends into the ear a sufficient amount, but without abutting against the tympanic membrane. The other function is that the shield acts to self-retain the tubing in the ear by snapping in place behind the tragus. This is an important aid in the use of air caloric stimulation. Apertures passing through the shield allow air to escape freely to prevent a build-up of pressure in the ear canal.

The above mentioned and other objects and features of the invention will become more apparent from the description of the apparatus in the following specification, taken in conjunction with the accompanying drawings, in which:

FIG. 1 is a pictorial representation of the air caloric stimulation system apparatus;

FIG. 2 is a pictorial representation of the air caloric delivery tube described;

FIG. 3 is an exploded view of the air caloric delivery tube of FIG. 2;

FIG. 4 is a schematic representation of the delivery tube attached to the ear of the patient for receiving air from a delivery nozzle; and FIGS. 5 A and B are embodiments of both sides of the shielded section of the delivery tube.

In the pictorial drawing of FIG. 1 the overall air caloric system apparatus is shown as 11. The control unit 12 includes a power off switch 14, a pilot light 16 for indicating when the power is on, a flow adjust control 17, which adjusts the flow of the air coming out of the delivery head 13 through the replaceable nozzle 18. The amount of air, of course, is monitored by the gauge accompanying the air flow adjust control 17. Temperature control knobs 19 and 21 along with the temperature meter 22 are further shown on the control unit 12. The timer control knob 23 controls elapsed time before a signal indicates that the end of the seqeunce of the delivery of air through the delivery head 13 and tube 18 has occurred.

When the signal sounds, the flow of air into the patient's ear is ideally stopped by removing the delivery tube from the head 13 at 28. Alternatively, the tube 18 is clamped prior to its removal from the ear.

The electrical and fluid connections between the head 13 and the control unit 12 are provided through a basic umbilical cord 24. The head is movable so that the air can be easily applied to each of the patient's ears as required through the air caloric delivery tube 18 which is replaceable. A plastic or rubber nipple nozzle shown at 28 is applied to the side 29 of head 13. The side 29 is one side of case 30 of the head. A handle 31 may be utilized; however, the handle is not necessary, since the head fits conveniently into the doctor or test administrator's hands.

FIG. 2 shows the details of the air caloric delivery tube 18. Therein is shown the nipple connecting portion of the delivery tube 18. This is shown as coupling means or portion 32a, and is preferrably of a harder material than the main tube portion 33, which is of smaller diameter soft polymeric silicate material. A handle section 34 is provided. Main tube portion 33 protrudes through handle section 34 and through shielded section 36 so that only an end or nozzle portion 37 of main tube portion 33 fits into the ear. End portion 37 is of proper length to assure its extending close to the tympanic membrane without impinging thereon. It has been found that the length of the tubing which properly fits into the ear is about 20 milimeters. This length assures that the end portion 37 will not reach the tympanic membrane in any adult ear, yet it will extend past the interior wall curvature as shown in FIG. 4 as 38. The tympanic membrane is shown as 39 in the schematic showing of FIG. 4.

As best shown in FIG. 5 the shielded section 36 also is a tubular section. The shield has a longitudinal aperture 41 therethrough. A transverse aperture 42 is machined into the tube-like shield 36 to enable end portion 37 of tube 33 to fit through aperture 42 and thereby pass through the shield 36. Two openings 44 and 45 on the end portion side of the shield allow free air escape from the canal into the longitudinal aperture 41, as well as two notches in the other side 46 and 47.

The handle section 34 is preferrably also a larger diameter plastic tube having longitudinal aperture 43 extending therethrough to enable main tube portion 33 to extend through apertures 43 and 42 the required distance so that end portion 37 extends into the inner ear of the patient.

At the tube end the sleeve 32a fits into head fitting 28, as shown in FIG. 3. An intermediate diameter connector tube 32 can be used to connect the smaller main tube portion 33 to nozzle connecting end 32a or the rigid portion 32a can be coupled right to main tube portion 33. Because of the section 32a which is rigid, the delivery tube can be easily inserted into the plastic or rubber delivery nozzle 28 of head 13, as shown in the cross-sectional schematic of FIG. 4. The main tube 33 is flexible so it must be short enough not to collapse, but long enough to prevent movements of the connector tube from being transferred to the nozzle or delivery end 37, where slight lateral movements can be painful to the ear canal when lying therein.

In use the delivery tube nozzle or end portion 37 is inserted into the ear before attaching it to the section 28. The end portion 37 is inserted into the canal 38 and the shield 36 is snapped into place behind the tragus of the ear 41. The tragus, of course, is that fleshy portion of the ear which extends over the opening into the inner ear. The shield is adjusted so that it lies inferior to the long crus 46 on the helix of the outer ear structure. The attachment in this position is self-retaining and immobile.

The air caloric stimulator is set at the appropriate temperature and volume flow and the delivery tube nozzle opening is slipped over the sleeve 32a of the connector tube 32. After the appropriate time period of air stimulation, an alarm rings and the tube is removed from delivery nozzle 28 of head 13. The delivery tube, however, can be left in the ear.

Appropriate ENG recordings are taken on a recorder, not shown. The air caloric stimulator is then switched to the next temperature setting and allowed to equilibrate while the patient is resting. The same ear can then be stimulated with the next temperature setting without removing the delivery tube apparatus. By this means hot and cold temperature stimulations can be carried out on each side, while inserting the tube only once in each ear. The delivery tube apparatus is then removed by gentle traction for cleaning and sterilizing prior to reuse.

The narrowing, silicone tubing coming from the delivery nozzle is flexible, and therefore, less traumatic in the ear canal than the previously used, more rigid, wider sized silicone tubing. The wider tubing at the nozzle end is rigid so that it will slide in and out of the delivery nozzle with ease.

While the principles of the invention have been described above in connection with the specific apparatus and applications, it is to be understood that this inventive description is given only by way of example, and not as a limitation on the scope of the invention.

I claim:

1. An air caloric delivery tube for use with air caloric stimulation systems used in measuring vestibular responses of patients comprising
    a main tube portion having a nozzle end for extending into the ear of a patient,
    said delivery tube including means for coupling to the air caloric stimulation systems which are equipped to supply air at controlled temperatures and flows to the ears of the patients,
    said coupling means including a rigid nipple,
    a nipple connecting tube joining said main tube portion, and said nipple,
    the inner diameter of said main tube portion being smaller than the inner diameter of said rigid nipple,
    shield means on said main tube portion removed from said nozzle end for locking said delivery tube in the ear of a patient with the shield means abutting the tragus of the patient's ear while preventing the nozzle end from impinging on the tympanic membrane of the patient,
    said shield means comprising a hollow cylindrical section, and
    the longitudinal axis of said cylindrical section being normal to the longitudinal axis of said means tube portion.

2. The air caloric delivery tube of claim 1 wherein said shield means includes a first shield aperture normal to the longitudinal axis of said cylindrical section of a size to enable passage therethrough of said nozzle end, and
    further shield means for enabling free passage of air through said shield means from the ear canal.

3. The air caloric delivery tube of claim 2 wherein handle means are provided for controlling said shield means and nozzle end.

4. The delivery tube of claim 3 wherein said handle means comprises a second cylindrical section surrounding said main tube portion,
    said second cylindrical section being of a larger diameter than said nozzle end,
    a handle means aperture extending axially through said second cylindrical section of a size to enable passage therethrough of said nozzle end, and
    said handle means at one end conforming to said shield means, whereby said handle means with said nozzle end therethrough in the assembled delivery tube is contiguous to said shield means.

5. The delivery tube of claim 1 wherein at least said nozzle end of the said delivery tube is fabricated from a soft pliable material.

6. The delivery tube of claim 1 wherein
    said nipple has a nipple aperature adapted to extend from said air caloric stimulation systems, and
    said connecting tube has a larger inner diameter than said main tube portion and a smaller outer diameter than the aperture of said apertured nipple.

* * * * *